(12) United States Patent
Kim (10) Patent No.: US 10,799,130 B2
(45) Date of Patent: Oct. 13, 2020

(54) DEVICE FOR EXTRACTION OF PEAKS FROM CONTINUOUS INTRACRANIAL PRESSURE WAVEFORM AND DETECTION METHOD FOR THE SAME

(71) Applicant: Korea University Research and Business Foundation, Seoul (KR)

(72) Inventor: Dong-Joo Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 252 days.

(21) Appl. No.: 15/567,858

(22) PCT Filed: Apr. 20, 2016

(86) PCT No.: PCT/KR2016/004132
§ 371 (c)(1),
(2) Date: Oct. 19, 2017

(87) PCT Pub. No.: WO2016/171476
PCT Pub. Date: Oct. 27, 2016

(65) Prior Publication Data
US 2018/0103862 A1  Apr. 19, 2018

(30) Foreign Application Priority Data
Apr. 21, 2015 (KR) .................. 10-2015-0055835

(51) Int. Cl.
*A61B 5/03* (2006.01)
*G06K 9/46* (2006.01)
(Continued)

(52) U.S. Cl.
CPC .............. *A61B 5/031* (2013.01); *A61B 5/021* (2013.01); *A61B 5/024* (2013.01); *A61B 5/0205* (2013.01);
(Continued)

(58) Field of Classification Search
CPC ....... A61B 5/031; A61B 5/0205; A61B 5/021; A61B 5/0452; A61B 5/024; A61B 5/7271; G06K 9/46
See application file for complete search history.

(56) References Cited

U.S. PATENT DOCUMENTS

| 2004/0158162 | A1* | 8/2004 | Narimatsu | ............. A61B 5/022 600/494 |
| 2007/0276264 | A1* | 11/2007 | Eide | ......................... A61B 3/16 600/485 |
| 2012/0101387 | A1* | 4/2012 | Ji | .......................... A61B 5/026 600/454 |

FOREIGN PATENT DOCUMENTS

| JP | 2004313468 A | 11/2004 |
| JP | 2011229767 A | 11/2011 |

(Continued)

OTHER PUBLICATIONS

Hu et al. 'Morpholigcal Clustering and Analysis of Continuous Intracranial Pressure' IEEE Trans Biomed Eng. Mar. 2009; 56(3): 696-705. (Year: 2009).*

*Primary Examiner* — Patrick Fernandes
(74) *Attorney, Agent, or Firm* — Fox Rothschild LLP (57) ABSTRACT

The present invention relates to a device and a method for detecting a peak of an intracranial pressure (ICP) waveform using a morphological feature of an arterial blood pressure waveform. A peak extracting method of an ICP waveform using a morphological feature of an arterial blood pressure waveform according to an aspect of the present invention includes: extracting a pulse onset from a continuous ICP waveform based on systolic peak from arterial blood pressure waveform; dividing individual ICP waveforms in the continuous ICP waveform based on the pulse onset; deriving a derivative value from each of the ICP waveforms to extract a peak, a trough, and a flat; calculating latencies from the (Continued)

pulse onset extracted in each of the ICP waveforms to the extracted peaks to cluster peaks with a similar time interval and generate a peak cluster; searching a notch from each of the ICP waveforms based on the latency of a dicrotic notch of the arterial blood pressure waveform; and extracting P1, P2, and P3 peaks from each of the ICP waveforms by referring to the searched notch of the ICP.

16 Claims, 8 Drawing Sheets

(51) Int. Cl.
*A61B 5/021* (2006.01)
*A61B 5/024* (2006.01)
*A61B 5/0205* (2006.01)
*A61B 5/00* (2006.01)

(52) U.S. Cl.
CPC ............ *A61B 5/743* (2013.01); *A61B 5/7425* (2013.01); *G06K 9/46* (2013.01); *A61B 5/4842* (2013.01); *A61B 5/7278* (2013.01)

(56) References Cited

FOREIGN PATENT DOCUMENTS

| KR | 20020002450 A | 1/2002 |
| KR | 20060111391 A | 10/2006 |
| KR | 20120058243 A | 6/2012 |

* cited by examiner

| Subject | P1 | P2 | P3 |
|---|---|---|---|
| Patient 1 | 0.985 | 0.999 | 0.910 |
| Patient 2 | 0.985 | 0.955 | 0.910 |
| Patient 3 | 0.995 | 0.975 | 0.960 |
| Patient 4 | 0.995 | 0.955 | 0.900 |
| Patient 5 | 0.999 | 0.945 | 0.870 |
| Patient 6 | 0.995 | 0.990 | 0.955 |
| Patient 7 | 0.985 | 0.975 | 0.880 |
| Patient 8 | 0.935 | 0.940 | 0.970 |
| Patient 9 | 0.985 | 0.985 | 0.805 |
| Patient 10 | 0.995 | 0.990 | 0.955 |

(b)

(c)

(d)

DEVICE FOR EXTRACTION OF PEAKS FROM CONTINUOUS INTRACRANIAL PRESSURE WAVEFORM AND DETECTION METHOD FOR THE SAME

TECHNICAL FIELD

The present document relates to a device and a method for extracting peaks from an intracranial pressure waveform using a morphological feature of an arterial blood pressure waveform.

BACKGROUND ART

Patients with brain damages are subjected to intracranial pressure (ICP) monitoring, in addition to cardiac and respiratory monitoring which are applied to general patients in the intensive care unit. The object of the ICP monitoring is to accurately identify the neuro-physiological status and observe a pathophysiological change of the brain to make the status of the brain an optimal steady state suitable for individual patients.

A waveform of the ICP has harmonics, which is similar to a heart beat or a respiration period and indirectly provides information on a cerebral blood vessel system. Three major peaks observed from the waveform of the ICP are sequentially denoted by P1 (percussion wave), P2 (tidal wave), and P3 (dicrotic wave) and have different physiological origins. Therefore, characteristics such as three peaks, an amplitude of a trough existing between the peaks and a latency from a pulse onset to the peak could be used to describe the status of intracranial compliance, cerebral autoregulation, etc. Therefore, it is very important to accurately recognize and analyze the characteristics.

However, it is difficult to accurately extract three peaks due to morphological diversity of the waveform. Therefore, efforts have been made to increase an accuracy of techniques for recognizing peaks P1, P2, and P2 through various studies.

Specifically, among related arts, US Unexamined Patent Application Publication No. 2011-0201961 (morphological clustering and analysis of ICP pulses, MOCAIP) provides a method for recognizing three sub peaks from monitored ICP waveform and observing morphological changes of the ICP waveform using a latency and an amplitude of the sub peaks.

However, according to the MOCAIP of the related art, in order to detect peaks of the ICP waveform, reference pulse library obtained by collecting data extracted from many patients is utilized. In the reference pulse library, information of the ICP waveform with various shapes is stored. As described above, the MOCAIP technique improves the accuracy of the peak detection by referencing the stored information. However, the morphology of the ICP waveform may vary depending on various intracranial conditions or brain diseases and a waveform which may be referenced to detect the peak may vary depending on a property of data to be analyzed. Therefore, according to the related art, a vast reference pulse library which is formed of various patient cases is required. Accordingly, efficiency is lowered in an offline environment in which the reference pulse library cannot be used. Further, in the related art, the peak is detected from the ICP pulse in which individual pulses of the recorded ICP waveform are averaged in order to reduce defects or noises of a signal. However, the averaged ICP pulse may not include the characteristics of the individual pulses which vary in real time. Therefore, the clinical application of the related art may be limited.

SUMMARY

Technical Problem

An object of the present solution is to provide a method for automatically extracting peaks P1, P2, and P3 from a continuous ICP waveform.

Another object of the present solution is to provide a method for extracting peaks from the ICP waveform with high accuracy without using a reference pulse library.

However, technical objects to be achieved by the present solution are not limited to the technical objects as described above and other technical objects may be present.

Technical Solution

As a technical solution for solving the technical problems, according to an aspect of the present solution, there is provided a peak extracting method of an ICP waveform using a morphological feature of an arterial blood pressure waveform including extracting a pulse onset from a continuous ICP waveform based on a systolic peak of an arterial blood pressure waveform; dividing individual ICP waveforms in the continuous ICP waveform based on the pulse onset; deriving a derivative value from each of the ICP waveforms to extract a peak, a trough, and a flat; calculating a latency from the pulse onset extracted in each of the ICP waveforms to the extracted peaks to cluster peaks with a similar latency value and generate a peak cluster; searching a notch from each of the ICP waveforms based on the latency of a dicrotic notch of the arterial blood pressure waveform; and extracting P1, P2, and P3 peaks from the ICP waveforms by referring to the searched notch of the ICP.

Further, according to another aspect of the present solution, there is provided a peak extracting device of an ICP waveform using a morphological feature of an arterial blood pressure waveform including: a memory in which a peak extracting application of an ICP waveform is stored; and a processing unit which is aligned to interface with the peak extracting application of an ICP waveform. In this case, the processing unit receives an arterial blood pressure waveform and an ICP waveform from a sensor unit according to the execution of the peak detection application of the ICP waveform. Next, the processing unit converts the received arterial blood pressure waveform and ICP waveform into digital data to store the converted digital data in the memory. Next, the processing unit extracts a pulse onset from a continuous ICP waveform based on a systolic peak of the arterial blood pressure waveform. Further, the processing unit divides individual ICP waveforms in the continuous ICP waveform based on the pulse onset and derives a derivative value from each of the ICP waveforms to extract a peak, a trough, and a flat. Next, the processing unit calculates a latency of the peak extracted from the pulse onset from extracted each of the ICP waveforms. Next, the processing unit clusters peaks with similar time intervals to generate a peak cluster, and searches a notch from each of the ICP waveforms based on the latency of a dicrotic notch of the arterial blood pressure waveform. Next, the processing unit extracts P1, P2, and P3 peaks from each of the ICP waveforms based on the searched notch of the ICP waveform.

Advantageous Effects

According to any one of the above-described solving means of the present solution, three peaks are automatically extracted from an ICP waveform so that the ICP waveform may be consistently and directly monitored.

Further, when three peaks are automatically extracted from an ICP waveform, three peaks may be extracted with a high accuracy without using a reference pulse library.

| Explanation of Reference Numerals and Symbols | |
|---|---|
| 100: Sensor Unit | 200: Memory |
| 300: Processing Unit | 400: Display |

DETAILED DESCRIPTION

Hereinafter, an exemplary embodiment of the present solution will be described more fully hereinafter to be easily carried out by those skilled in the art. However, the present solution can be realized in various different forms, and is not limited to the exemplary embodiments described herein. Accordingly, the drawings and description are to be regarded as illustrative in nature and not restrictive. Like reference numerals designate like elements throughout the specification.

Throughout this specification and the claims that follow, when it is described that an element is "coupled" to another element, the element may be "directly coupled" to the other element or "electrically coupled" to the other element through a third element. In addition, unless explicitly described to the contrary, the word "comprise" and variations such as "comprises" or "comprising", will be understood to imply the inclusion of stated elements but not the exclusion of any other elements.

Hereinafter, a device and a method of extracting peaks of an ICP waveform using a morphological feature of an arterial blood pressure waveform will be described in detail with reference to the drawings.

Figure 1:
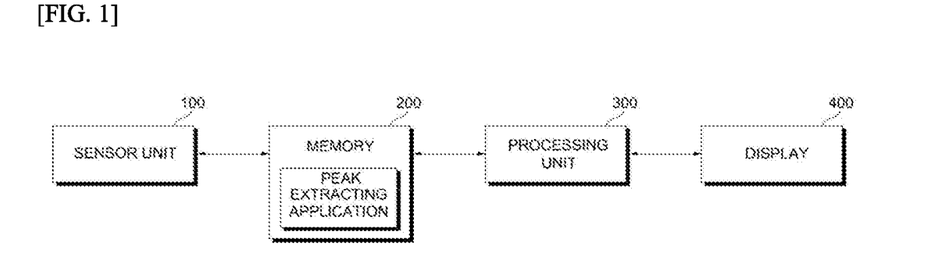
FIG. 1 schematically illustrates a peak extracting device of an ICP waveform using a morphological feature of an arterial blood pressure waveform.

FIG. 1 schematically illustrates a peak extracting device of an ICP waveform using a morphological feature of an arterial blood pressure waveform.

Referring to FIG. 1, a peak extracting device of an ICP waveform using a morphological feature of an arterial blood pressure waveform includes a sensor unit 100, a memory 200, a processing unit 300, and a display 400. In this case, the sensor unit 100 and the display unit 400 may be included in the peak extracting device of an ICP waveform using a morphological feature of an arterial blood pressure waveform or separately provided outside a feature detecting device of an arterial blood pressure waveform.

The sensor unit 100 includes an analog amplifier (not illustrated) and a digital converter (not illustrated) and measures an arterial blood pressure or an ICP to convert the arterial blood pressure or the ICP into a digital signal.

In the memory 200, a peak extracting application of an ICP waveform may be stored and arterial blood pressure waveform data and ICP waveform data which are converted into digital signals may be stored. In this case, the memory 200 includes an arbitrary method for storing information such as a computer readable command, a data structure, a program module, and other data or a volatile and non-volatile, a removable and non-removable medium which is implemented by an arbitrary method or a technique. For example, the memory 200 includes a NAND flash memory such as a read only memory (ROM), a random access memory (RAM), a magnetic tape, a magnetic disk, a flash memory, an optical data storage device, a compact flash (CF) card, a secure digital card, a memory stick, a solid state drive (SSD), and a micro SD card and a magnetic computer storage device such as a hard disk drive (HDD).

The processing unit 300 derives a derivative value from the arterial blood pressure waveform data and the ICP waveform data stored in the memory 200 according to execution of the peak extracting application of the ICP waveform to extract a morphological feature of the arterial blood pressure waveform and extract three peaks from the ICP waveform.

The display 400 may display an ICP waveform measured by the sensor unit 100 and three peaks on the ICP waveform extracted by the processing unit 300 in real time. Further, the display 400 may display points where the peaks are located by different colors.

Figure 2:
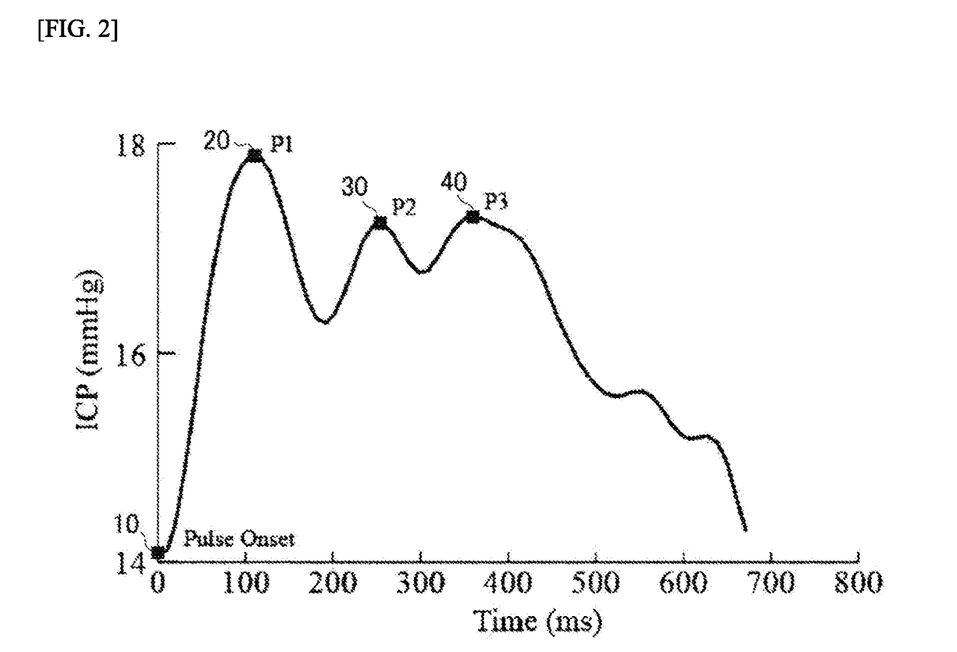
FIG. 2 illustrates three peaks of an ICP waveform which is considered in a scenarios of the present solution.

FIG. 2 illustrates three peaks of an ICP waveform which is considered in a scenario of the present solution.

Referring to FIG. 2, the ICP waveform considered in the scenarios of the present solution includes three sub pulses P1, P2, and P3. In this case, crests of individual pulses are defined as a P1 peak, a P2 peak, and a P3 peak in an order of the peaks appearing in the waveform. Three peaks in the ICP waveform include information on an intracranial compliance and a cerebral vasculature.

Specifically, a P1 pulse is a first pressure wave appearing when a choroid plexus beats in a systole of the heart and is also referred to as a percussion wave. Next, a P2 pulse which appears after the P1 pulse is generated by a rebound phenomenon of the vein. Generally, in a normal situation, an energy generated by the rebound phenomenon of the vein is absorbed so that an amplitude of the P2 peak is lower than an amplitude of the P1 peak. However, when an intracranial compliance is reduced, the rebound phenomenon is severe and the amplitude of the P2 peak is increased. Sometimes, the amplitude of the P2 peak may be larger than the amplitude of the P1 peak. Therefore, a reversal phenomenon in which the amplitude of the P2 peak is larger than the amplitude of the P1 peak indicates reduction of the intracranial compliance. Further, at the end of the ventricular systole, an aortic valve is closed and a notch appears in the ICP waveform at the same timing as a time when a dicrotic notch is observed from the arterial blood pressure waveform. Therefore, the P3 pulse is generated as the ventricle enters the diastole after the notch appears in the waveform of the ICP.

As described above, when blood flows into the brain due to the heart beat, the ICP waveform also varies due to vibration of a blood flow. That is, the ICP waveform is related to a waveform of the arterial blood pressure. This is because a cerebral blood volume varies due to the heart beat and thus the cerebral pressure is changed.

Further, in order to determine a goal of a treatment for patients with brain damages, it is very important to identify ranges of a blood pressure and a cerebral perfusion pressure for determining whether cerebral autoregulation is maintained in the patients with brain damages. However, it is difficult to figure out whether the cerebral autoregulation of individual patients is maintained and determine an adjustable range of the pressure. This is because in order to determine the ranges of the blood pressure and the cerebral perfusion pressure where the cerebral autoregulation is theoretically maintained, information on the arterial blood pressure and the cerebral blood flow is required, but it is difficult to obtain information on continuous cerebral blood flow. However, in the case of patients who lose the cerebral autoregulation, when the blood pressure rises, the cerebral blood flow immediately rises, which leads to a direct rise of the cerebral pressure. Therefore, when information on the cerebral pressure is provided, it is possible to figure out whether the cerebral autoregulation is maintained through a relationship between the blood pressure and the cerebral pressure. However, in the current clinical practice, due to technical limitations, the shape of the ICP waveform is not specifically considered and an analysis of a monitoring result of the ICP waveform is limited to consider an average of the measured ICPs.

Therefore, the peak extracting device of an ICP waveform using a morphological feature of an arterial blood pressure waveform provides a method for automatically searching three of P1, P2, and P3 waveforms from the ICP waveform and calculating information on latencies of peaks of the waveforms and amplitudes of the waveforms. Further, it is possible to derive various variables such as morphological features of the arterial blood pressure waveform, a latency from a pulse onset of the ICP waveform to the P1, P2, and P3 peaks and an amplitude and analyze correlation of the variables. Therefore, it is possible to extract peaks of the ICP waveform and monitor a changing status without using a reference pulse library extracted from the patients which is required for a technique of the related art which analyzes the ICP waveform. Further, it is possible to measure deterioration of the intracranial compliance of the patients with brain damages and a damage of a self-regulation function of the patients with brain damages, which is useful for predicting whether the patients with brain damage is improved.

Hereinafter, a peak detecting method of an ICP waveform using a morphological feature of an arterial blood pressure waveform will be described in detail with reference to FIG. 3.

Figure 3:
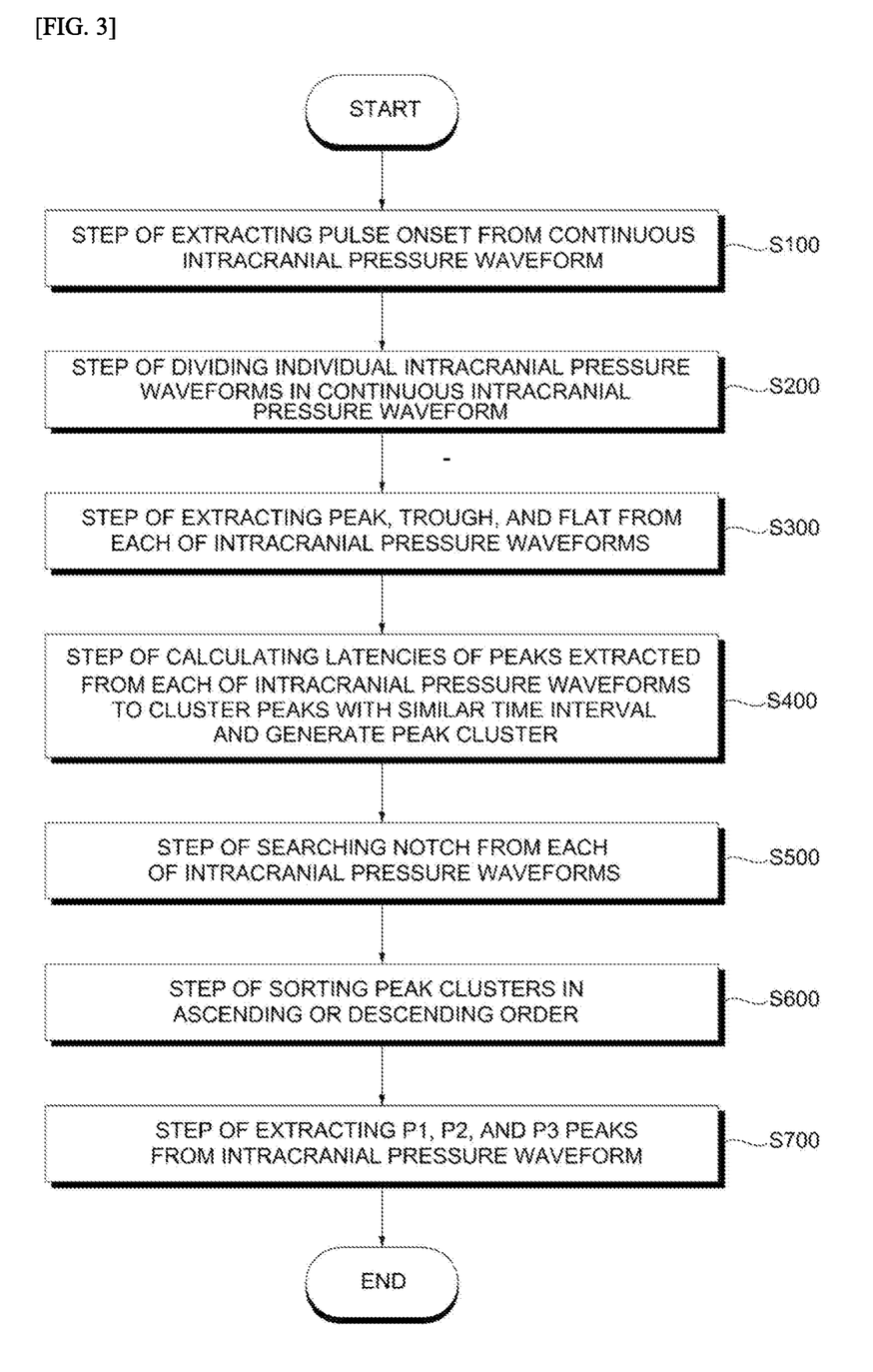
FIG. 3 is a flowchart for specifically explaining a peak extracting method of an ICP waveform using a morphological feature of an arterial blood pressure waveform.

FIG. 3 is a flowchart for specifically explaining a peak extracting method of an ICP waveform using a morphological feature of an arterial blood pressure waveform.

Referring to FIG. 3, the peak extracting method of an ICP waveform using a morphological feature of an arterial blood pressure waveform includes a step s100 of extracting a pulse onset from a continuous ICP waveform, a step s200 of dividing individual ICP waveforms in the continuous ICP waveform, a step s300 of extracting a peak, a trough, and a flat from each of the ICP waveforms, a step s400 of calculating latencies of the peaks extracted from each of the ICP waveforms to cluster peaks with similar time interval and generate a peak cluster, a step s500 of searching a notch from each of the ICP waveforms, a step s600 of sorting peak clusters in an ascending or descending order, and a step s700 of extracting P1, P2, and P3 peaks from the ICP waveform.

First, in the step s100 of extracting a pulse onset from continuous ICP waveform, the processing unit 300 extracts the pulse onset from the continuous ICP waveform based on search information of a systolic peak of the arterial blood pressure waveform.

Figure 4:
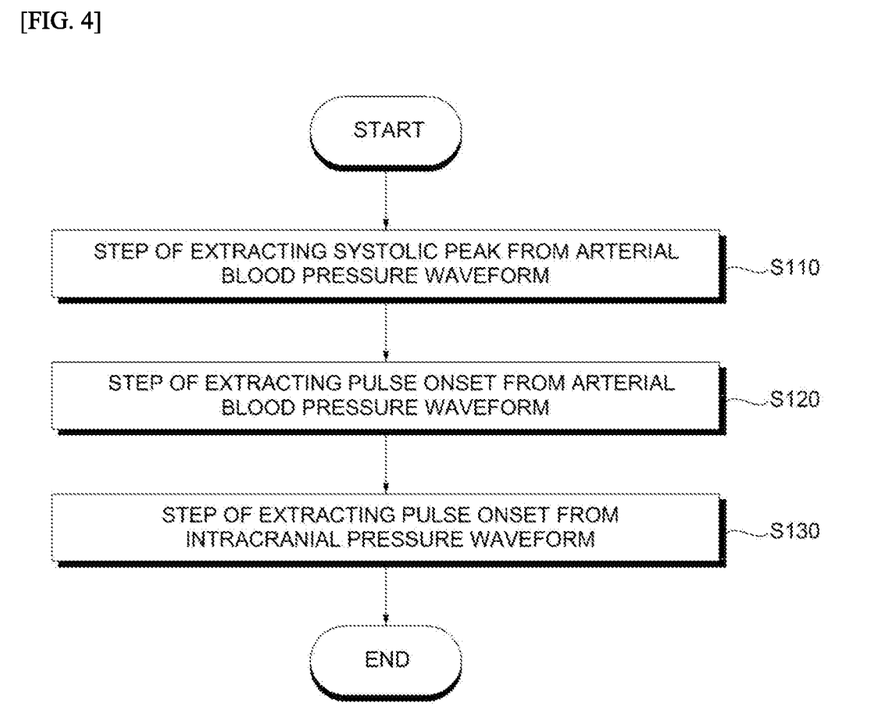
FIG. 4 is a flowchart for specifically explaining a step of extracting a pulse onset from a continuous ICP waveform.

FIG. 4 is a flowchart for specifically explaining a step of extracting a pulse onset from a continuous ICP waveform.

Referring to FIG. 4, the step of extracting a pulse onset from a continuous ICP waveform includes a step s110 of extracting a systolic peak from the arterial blood pressure waveform, a step s120 of extracting a pulse onset from the arterial blood pressure waveform, and a step s130 of extracting a pulse onset from the ICP waveform.

According to the present solution, in the step s110 of extracting a systolic peak from the arterial blood pressure waveform, the processing unit 300 derives a derivative value from the arterial blood pressure waveform and calculates a maximum value and a mean value of the arterial blood pressure waveform during an arbitrary time period at the beginning of the analysis. Next, the processing unit collects peaks which exceed the calculated mean value and are close to the maximum value in a time window. In this case, when it is assumed that a j-th point of the arterial blood pressure waveform is $A_j$ and a pressure value is $P_{A,j}$, the collected peak may be a point which satisfies that $P_{A,j-1} < P_{A,j}$ and $P_{A,j} > P_{A,j+1}$.

In the meantime, a length of the time window depends on an arbitrary time for analyzing the maximum value and the mean value. For example, when the candidates of the systolic peak are collected after analyzing the maximum value and the mean value in a waveform existing within three seconds, as the collected candidates of the systolic peak are increased, the length of the time window has a range from a minimum of 3 seconds to a maximum of 30 seconds.

Next, the processing unit 300 calculates a mean time interval $mean\lambda_j$ of peaks collected in the time window and a mean pressure $meanP_j$. Here, the time interval $\lambda_{A,j}$ refers to a time interval between a j-th peak collected in the time window and a previous peak.

Next, the processing unit 300 extracts the systolic peaks based on the mean time interval $mean\lambda_j$ and the mean pressure value $meanP_j$ calculated in the time window. In this case, as the systolic peaks, j-th peaks which satisfy $|meanP_{A,j} - P_{A,j}| < meanP_{A,j} * 0.15$ and $|mean\ \lambda_{A,j} - \lambda_{A,j}| < mean\ \lambda_{A,j} * 0.15$ may be selected from the candidates of the systolic peaks extracted in the time window.

Next, in the step s120 of extracting a pulse onset from the arterial blood pressure waveform, the processing unit 300 extracts trough points which appears before a maximum slope of the derivative, that is, exists immediately before the systolic peak 20 as the pulse onset.

Next, in the step s130 of extracting a pulse onset from an ICP waveform, the processing unit 300 extracts the pulse onset from the continuous ICP waveform based on search information of a systolic peak of the arterial blood pressure waveform. According to the present solution, when it is assumed that a measurement time of a systolic peak of the arterial blood pressure waveform is $\mu_{A,j}$, the processing unit 300 calculates a minimum value $minP_I$, a maximum value $maxP_I$, and a mean value $meanP_I$ of the pressure value $P_{I,j}$ of the ICP waveform existing between $\mu_{A,j}$ and $\mu_{A,j+1}$. Thereafter, when it is searched in a time reverse order from a measurement time of the ICP waveform at a point where $maxP_I$ is measured to $\mu_{A,j}$, the processing unit extracts a trough $I_k$ of the ICP waveform which satisfies Equation 1 as a pulse onset of the ICP waveform.

$$|P_{I,k} - minP_I| < |P_{I,k} - meanP_I| \quad \text{[Equation 1]}$$

Referring to FIG. 3 again, during the peak extracting process of an ICP waveform using a morphological feature of an arterial blood pressure waveform according to the present solution, the processing unit 300 divides individual ICP waveforms in the continuous ICP waveform using an extracted pulse onset after extracting a pulse onset from the ICP waveform (s200). That is, the processing unit 300 divides waveforms divided by the pulse onset extracted in step s100 and a next pulse onset. In this case, data of the ICP waveform existing between pulse onsets may be represented by one vector and individual data may be represented by $M_i$, I=1, ... n without dividing the arterial blood pressure waveform and the ICP waveform. Here, n refers to a last waveform of the arterial blood pressure waveform and the ICP waveform.

In the meantime, the peak extracting method of an ICP waveform using a morphological feature of an arterial blood pressure waveform according to the present solution may linearly interpolate the number of data in $M_i$ by 64. In this case, data existing in an i-th waveform $M_i$ may be described by a two-dimensional point and may be represented by the following Equation 2.

$$x_{i,j} = \{t_{i,j}, f(t_{i,j})\} \quad \text{[Equation 2]}$$

Here, $t_{i,j}$ represents a time domain and $f(t_{i,j})$ represents a pressure domain.

Further, the peak extracting method of an ICP waveform using a morphological feature of an arterial blood pressure waveform may further include a step of filtering a waveform which has an inappropriate pulse onset after the step of dividing individual ICP waveforms in a continuous ICP waveform. In the step of filtering a waveform which has an inappropriate pulse onset, specifically, a cardiac cycle which is calculated by a value of $t_{i,64} - t_{i,j}$ may be used. Therefore, a mean cardiac cycle of previous three waveforms and subsequent three waveforms for every waveform is calculated and waveforms having a cardiac cycle which is out of the range of ±MCC*0.15 are determined to be inappropriate and excluded. Thereafter, it passes through a low pass filter to remove a noise of data. For example, the low pass filter may be 10 Hz, but is not limited thereto.

Next, in the peak extracting method of an ICP waveform using a morphological feature of an arterial blood pressure waveform, a peak, a trough, and a flat are extracted from each of the ICP waveforms (s300). Here, the flat is not a peak in the ICP waveform, but indicates a point where a waveform is flat or a pressure value is slightly decreased or increased.

Figure 5:
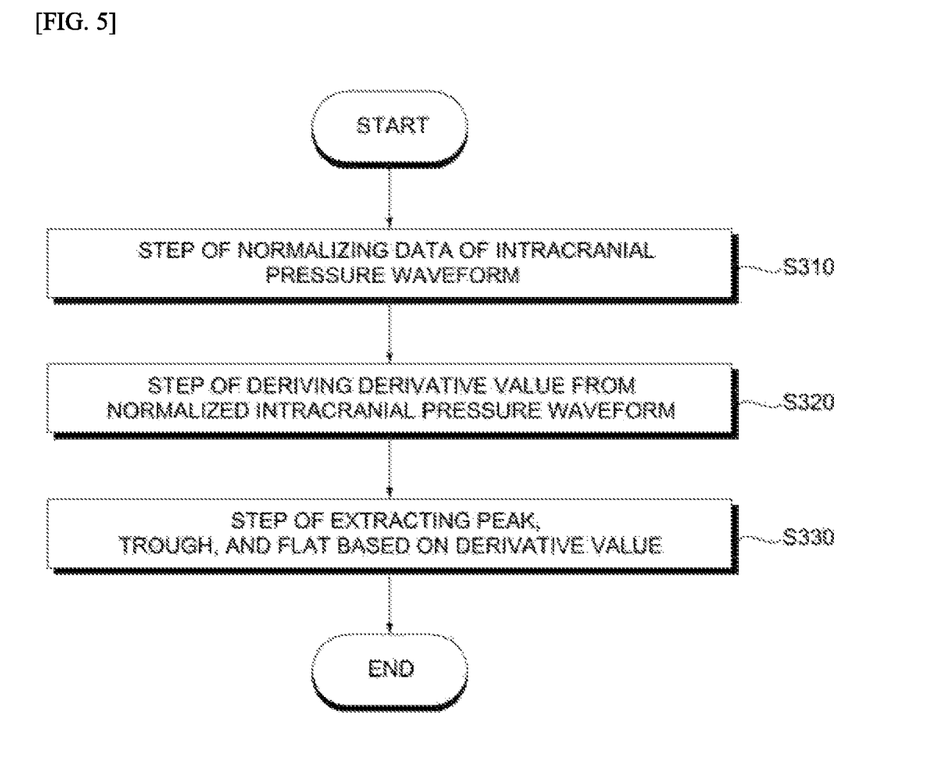
FIG. 5 is a flowchart for specifically explaining a step of extracting a peak, a trough, and a flat from an ICP waveform.

FIG. 5 is a flowchart for specifically explaining a step of extracting a peak, a trough, and a flat from an ICP waveform.

Referring to FIG. 5, the step of extracting a peak, a trough, and a flat from an ICP waveform includes a step s310 of normalizing data of the ICP waveform, a step s320 of deriving a derivative value from the normalized ICP waveform, and a step s330 of extracting a peak, a trough, and a flat based on the derivative value.

According to the present solution, in the step s310 of normalizing data of the ICP waveform, a maximum value and a minimum value of the pressure domain in Mi are derived and the minimum value of a pressure for every waveform is replaced with 0 and the maximum value is replaced with 100. Thereafter, each $x_{i,j}$ is transformed into $\alpha_{i,j} = \{\tau_{i,j}, f(\tau_{i,j})\}$ through normalization and $\tau_{i,j}$ and $f(\tau_{i,j})$ are represented by Equations 3 and 4, respectively.

$$\tau_{i,j} = 100 \times \frac{t_{i,j} - t_{i,1}}{t_{i,64} - t_{i,1}} \quad \text{[Equation 3]}$$

$$f(\tau_{i,j}) = 100 \times \frac{f(t_{i,j}) - \min_i\{f(t_{i,j})\}}{\max_i\{f(t_{i,j})\} - \min_i\{f(t_{i,j})\}} \quad \text{[Equation 4]}$$

Next, the derivative value may be derived from the normalized ICP waveform (s320). Since the ICP waveform is interpolated with regular intervals, the derivative value may be derived using a central difference method. Specifically, when a length between arbitrary two points existing in the waveform is defined as $h = \tau_{i,j} - \tau_{i,j-1}$, a method for deriving a derivative value is represented by Equation 5.

$$f'(\tau_{i,j}) = \frac{-f(\tau_{i,j+2}) + 8f(\tau_{i,j+1}) - 8f(\tau_{i,j-1}) + f(\tau_{i,j-2})}{12h}, \quad \text{[Equation 5]}$$
$$j = 3, \ldots, 62$$

In the meantime, in order to derive the derivative value for one data value, the above-described method using a central difference method requires previous two data values and subsequent two data values. Therefore, when there are no two or more previous data and two or more subsequent data, the derivative value may be derived using Equation 6.

$$f'(t_{i,j}) = 0, j \neq 3, \ldots, 62 \quad \text{[Equation 6]}$$

Next, in the step s330 of extracting a peak, a trough, and a flat based on the derivative value, when both $f'(\tau_{i,j-1}) > 0$ and $f'(\tau_{i,j}) < 0$ are satisfied, if $f(\tau_{i,j-1}) < f(\tau_{i,j})$, the processing unit 300 extracts $\alpha_{i,j}$ as a peak and if $f(\tau_{i,j-1}) > f(\tau_{i,j})$, extracts $\alpha_{i,j-1}$ as a peak.

Further, when both $f'(\tau_{i,j-1}) < 0$ and $f'(\tau_{i,j}) > 0$ are satisfied, if $f(\tau_{i,j-1}) > f(\tau_{i,j})$, the processing unit extracts $\alpha_{i,j}$ as a trough and if $f(\tau_{i,j-1}) < f(\tau_{i,j})$, extracts $\alpha_{i,j-1}$ as a trough.

In the meantime, when all the seven points from $\alpha_{i,j-3}$ to $\alpha_{i,j+3}$ are not a peak nor a trough and a condition of $|f'(\tau_{i,j})| < 1$ is satisfied, the processing unit 300 extracts $\alpha_{i,j}$ as a flat. In this case, flats may be continuously set in several points.

As described above, in the step of extracting a peak, a trough, and a flat from an ICP waveform, major points such as a peak, a trough, and a flat are extracted for all points of the normalized ICP waveform. When $\alpha_{i,j}$ is extracted as a major point which is any one of a peak, a through, and a flat, $x_{i,j}$ which is a data point before the normalization corresponding to the extracted major point is also extracted as a major point.

Further, the method may include a step of extracting a major point such as a peak, a trough, and flat also from the arterial blood pressure waveform using a method for extracting a peak, a trough, and a flat from the ICP waveform. Therefore, all major points may be extracted from data of the arterial blood pressure waveform and the ICP waveform according to the above-described method Referring to FIG. 3 again, in the peak extracting method of an ICP waveform using a morphological feature of an arterial blood pressure, after the step s300 of extracting a peak, a trough, and a flat from each of the ICP waveforms, latencies of the peaks extracted from each of the ICP waveforms are calculated to cluster peaks with similar latency and generate a peak cluster (s400).

Figure 6:
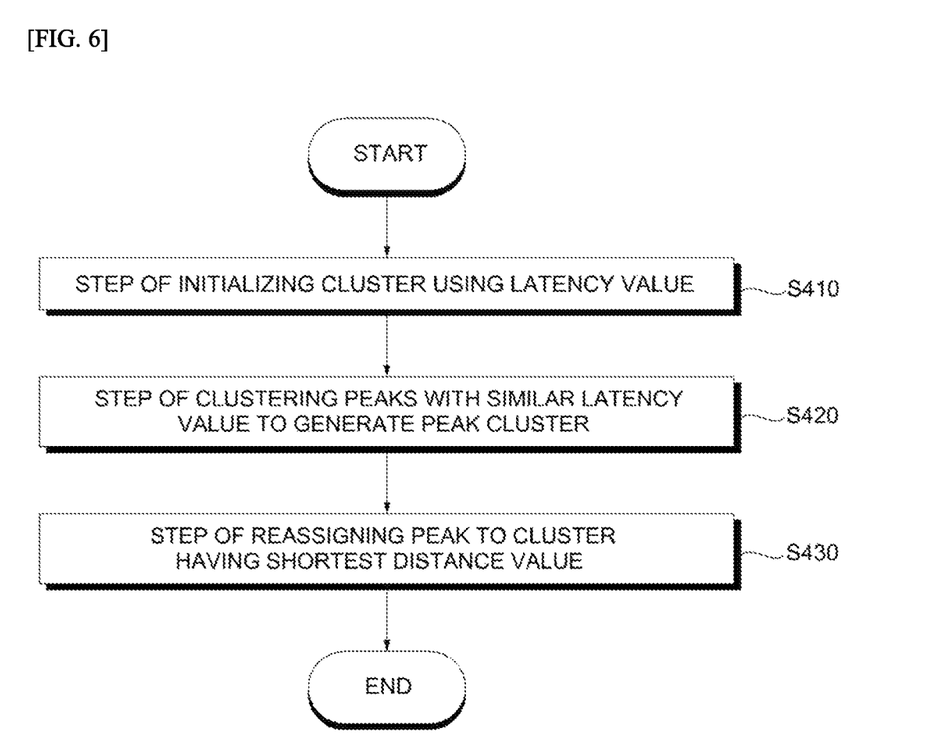
FIG. 6 is a flowchart for specifically explaining a step of calculating latencies of peaks extracted from ICP waveforms to group peaks with similar latency values and cluster with a peak cluster.

FIG. 6 is a flowchart for specifically explaining a step s400 of calculating latencies of peaks extracted from each of the ICP waveforms to cluster peaks with similar latency values to generate a peak cluster.

Referring to FIG. 6, the step s400 of calculating latencies of peaks extracted from the ICP waveforms to cluster peaks with similar latency values to generate a peak cluster includes a step s410 of initializing the cluster using the latency value, a step s420 of clustering peaks with similar latency values to generate a peak cluster, and a step s430 of reassigning a peak to a cluster having a shortest distance value.

First, in the step of initializing the cluster using the latency value, the processing unit 300 calculates a distance between most recent elements $x_{i,j}$ which are input to a k-th cluster $C_k$. In this case, the distance $D_k(x_{i,j})$ between most recent elements $x_{i,j}$ which are input to a k-th cluster $C_k$ may be calculated by the following Equation 7.

$$D_k(x_{i,j}) = \begin{cases} |L(y_{k,p}) - L(x_{i,j})|, \ p = 1 \\ \left|\frac{L(y_{k,p}) + L(y_{k,p-1})}{2} - L(x_{i,j})\right|, \ p \neq 1 \end{cases} \quad \text{[Equation 7]}$$

Here, $L(x_{i,j})$ represents a time interval from a pulse onset to $x_{i,j}$ and is calculated by Equation 8.

$$L(x_{i,j}) = t_{i,j} - t_{i,1} \quad \text{[Equation 8]}$$

Further, $L(y_{k,p})$ represents a time interval of the last element included in the k-th cluster $C_k$.

In the peak extracting method of an ICP waveform using a morphological feature of an arterial blood pressure waveform, the processing unit 300 calculates the distance $D_k(x_{i,j})$ between most recent elements $x_{i,j}$ which are input to the k-th cluster $C_k$ using Equation 7 and determine whether to include $x_{i,j}$ in the existing cluster or generate a new cluster based on the distance. In this case, a branch point q for generating a new cluster may be initialized to be 0.1 second. Further, when a minimum value of $D_k(x_{i,j})$ is larger than a determined branch point q, a new cluster is repeatedly generated to assign a peak $x_{i,j}$ thereto so that all peaks may be assigned to the cluster. Next, when the number of generated clusters is 5 or more, the branch point q is increased to be q+0.01 and the above-described processes are repeated. When the increased branch point q is 0.2 seconds or higher or the number of clusters is less than 5, the step of initializing a cluster ends.

Next, in the step s420 of clustering peaks with similar latency values to generate a peak cluster, the processing unit 300 calculates a mean mean($C_k$) of time intervals of the initialized clusters using Equation 9.

$$\text{mean}(C_k) = \frac{\sum_{u=1}^{p} L(y_{k,u})}{p} \quad \text{[Equation 9]}$$

According to the present solution, a distance between $C_k$ and $x_{i,j}$ is newly defined using the calculated mean time interval of the cluster using the Equation 9 and the newly defined distance $D'_k$ is represented by Equation 10.

$$D'_k(x_{i,j}) = |\text{mean}(C_k) - L(x_{i,j})| \quad \text{[Equation 10]}$$

Next, in the step s430 of reassigning a peak to a cluster having a shortest distance value, the processing unit 300 determines a cluster based on the newly defined $D'_k(x_{i,j})$ to reassign $x_{i,j}$. In this case, in a method for determining a cluster where the peak is to be reassigned, distances between all clusters and $x_{i,j}$ are calculated so that a cluster with a shortest distance may be determined. Therefore, some peaks may be assigned to the existing cluster. However, when the existing cluster does not have a shortest distance value, the peak may be reassigned to a cluster with a shortest distance. Therefore, an accuracy for classifying clusters may be increased.

Next, in the step s500 of searching a notch from each of the ICP waveforms, the processing unit 300 extracts a dicrotic notch of the arterial blood pressure waveform and searches a notch from the ICP waveform using the dicrotic notch.

The processing unit 300 may extract any one of a trough and a flat among major points obtained from the arterial blood pressure waveform as a dicrotic notch. Specifically, the processing unit 300 sets a range from $\mu_{A,j}+0.1(\mu_{A,j+1}-\mu_{A,j})$ to $\mu_{A,j}+0.25(\mu_{A,j+1}-\mu_{A,j})$ as a search window and searches a point of an arterial blood pressure waveform which satisfies Equation 11 to extract the point as a candidate of the dicrotic notch. In this case, $\mu_{A,j}$ represents a measurement time of a systolic peak $A_j$ of the arterial blood pressure waveform having a pressure value of $P_{A,j}$ and Equation 11 is represented below.

$$-0.05 \times \frac{P_{A,j}}{(\mu_{A,j+1} - \mu_{A,j})} < f'(A_j) < 0 \quad \text{[Equation 11]}$$

Next, the processing unit 300 extracts a point having a smallest pressure value among the extracted candidates of dicrotic notches as a dicrotic notch and calculates a measuring time interval $L_n$ from the pulse onset of the arterial blood pressure waveform to the dicrotic notch.

Generally, a notch existing between the P2 peak and the P3 peak of the ICP waveform is represented at a similar timing to a timing of the dicrotic notch of the arterial blood pressure waveform. Therefore, according to the method for searching a notch from each of the ICP waveforms, the notch of the ICP waveform is extracted using the calculated $L_n$. More specifically, the processing unit 300 extracts a trough which is the closest to a timing calculated by adding $L_n$ to a timing where the pulse onset of the ICP waveform extracted in the step s100 of extracting a pulse onset exists, as a notch of the ICP waveform. At this time, since there may be no notch of the ICP waveform in some cases, the searching may be performed only within a time window corresponding to 10% of a length of a cardiac cycle of the waveform.

Next, the processing unit 300 sorts the clustered peak clusters in an ascending or descending order (s600).

Next, in the step s700 of extracting P1, P2, and P3 peaks from the ICP waveform, peaks are extracted from the sorted peak clusters to be extracted as P1, P2, and P3 peaks. Specifically, when the notch of the ICP waveform is founded in step s500, the processing unit 300 sorts the peak clusters in an ascending or descending order and extracts the P1 peak based thereon. For example, the processing unit 300 sorts the peak clusters in an ascending order from a cluster having a smaller mean value and extracts a peak which is assigned to a first cluster according to the sorting order as P1. Next, the processing unit 300 searches peaks before and after the notch with respect to the extracted notch of the ICP waveform and extracts the peak before the notch as a P2 peak and the peak after the notch as a P3 peak.

In contrast, when the notch of the ICP waveform is not found in step s600, the processing unit 300 may extract P1, P2, and P3 peaks from the sorted peak cluster. For example, similarly to the above-described method, when the peak clusters are sorted in an ascending order from a cluster having a smaller mean value and the processing unit may extract a peak which is assigned to a first cluster according to the sorting order. Further, the processing unit may extract a peak assigned to a second cluster as P2 and a peak assigned to a third cluster as P3.

However, exceptionally, when a mean time interval between the peaks assigned to the first cluster and the pulse onset of the ICP waveform is 200 ms or longer, even though the cluster is the first cluster, the peak is extracted as P2. This is a reference made by referring to 233.6±27.7 ms which is a mean time interval between the P2 peak of the ICP waveform and the pulse onset researched by Kasprowics M et al. (2012). In this case, a peak assigned to the second cluster is automatically extracted as P3.

Further, when two or more peaks are assigned to the same cluster in one waveform, that is, peaks which are candidates of the P1, P2, and P3 peaks are two or more, a peak having the shortest time interval from the pulse onset of the ICP waveform may be selected.

Furthermore, when any one of P1, P2, and P3 is not extracted from one waveform, the peak may be replaced with one of flats. Specifically, the processing unit 300 searches a flat satisfying $D'_k(x_{i,j})<0.1$ among points $x_{i,j}$ determined as flats in $M_j$. Thereafter, when k is 1, $x_{i,j}$ of the flat is replaced with P1, when k is 2, $x_{i,j}$ is replaced with P2, and when k is 3, $x_{i,j}$ is replaced with P3.

In the meantime, the peak extracting method of an ICP waveform using a morphological feature of an arterial blood pressure waveform may further include a step of calculating any one of amplitudes of P1, P2, and P3 peaks, a latency from the pulse onset of the ICP waveform to P1, P2, and P3 peaks, and the number of P1, P2, and P3 peaks extracted from the ICP waveform, after the step s700 of extracting P1, P2, and P3 peaks from the ICP waveform. Next, the method may further include a step of morphologically analyzing the ICP waveform according to a calculated result to determine a prognosis of the patients with brain damages. In this case, the prognosis of the patients with brain damages is to determine whether the intracranial compliance of the patients with brain damages is deteriorated or cerebral autoregulation of the patients with brain damages is normal.

Specifically, the peak extracting method of an ICP waveform using a morphological feature of an arterial blood pressure waveform may be applied to a signal obtained from a patient with actual traumatic brain damage to calculate variables required to describe a condition of the patient. As one exemplary scenario, a ratio of waveforms in which P1 is the largest, a ratio of waveforms in which P2 is the largest, and a ratio of waveforms in which P3 is the largest from the ICP waveforms using amplitudes of P1, P2, and P3 and the ratios are referred to as a P1 ratio, a P2 ratio, and a P3 ratio. Next, as a result of analyzing a correlation between the P1 ratio, the P2 ratio, and the P3 ratio and the prognosis of the patient with a brain damage through Mann-Whitney U test, the P1 ratio of a survived patient is higher than that of a dead patient (p-value <0.0001). In contrast, the P2 ratio is statistically significantly higher in the dead patient (p-value <0.004). This may be an example to prove a result of a previous study in which as the intracranial compliance is deteriorated, P2 is increased and P1 is decreased. Therefore, it suggests that the present solution is used to monitor whether the intracranial compliance of the patient is deteriorated.

As another exemplary scenario, the ICP waveform of the ICP of patients with brain damages is divided and peaks are detected from each of the ICP waveforms by the peak extracting method of an ICP waveform using a morphological feature of an arterial blood pressure waveform. Next, the number of peaks in one ICP waveform is calculated using the peaks detected from the ICP waveform. Further, as a result of analyzing the correlation between the calculated result and the intracranial compliance of the patients with brain damage, as described above, as the intracranial compliance of the patient is deteriorated, the number of P1 peaks is reduced and the number of P2 peaks is increased. However, in the related art, only the P2 peak is observed in one ICP waveform. As derived by the present solution, when a threshold of a ratio of waveforms having only one peak is 20%, a positive predictive value for mortality prediction of a patient is approximately 77%. In other words, it means that 77% of patients with a ratio of a waveform having only one peak which exceeds 20% actually died. This is an example proving that it is possible to diagnose a status in the brain of the patient using intuitive and understandable variables.

The deterioration of the intracranial compliance may cause a volume change in the brain such as brain tumors, brain edema, and hematoma to lead to increase of the ICP. That is, since this may lead to the patient's death, the intracranial compliance is an important factor which needs to be observed to diagnose a status of the patient with brain damage. Therefore, when the P1, P2, and P3 peaks are accurately recognized by the automated method by the present solution, this may be expected to contribute prediction of the progress or death of the patient.

As described above, the peaks are automatically extracted from the continuous ICP waveform using a morphological feature of the arterial blood pressure waveform, so that it is possible to consistently and directly monitor an ICP waveform.

Further, when three peaks are automatically extracted from the ICP waveform, three peaks may be extracted with a high accuracy without using a reference pulse library.

Figure 7:
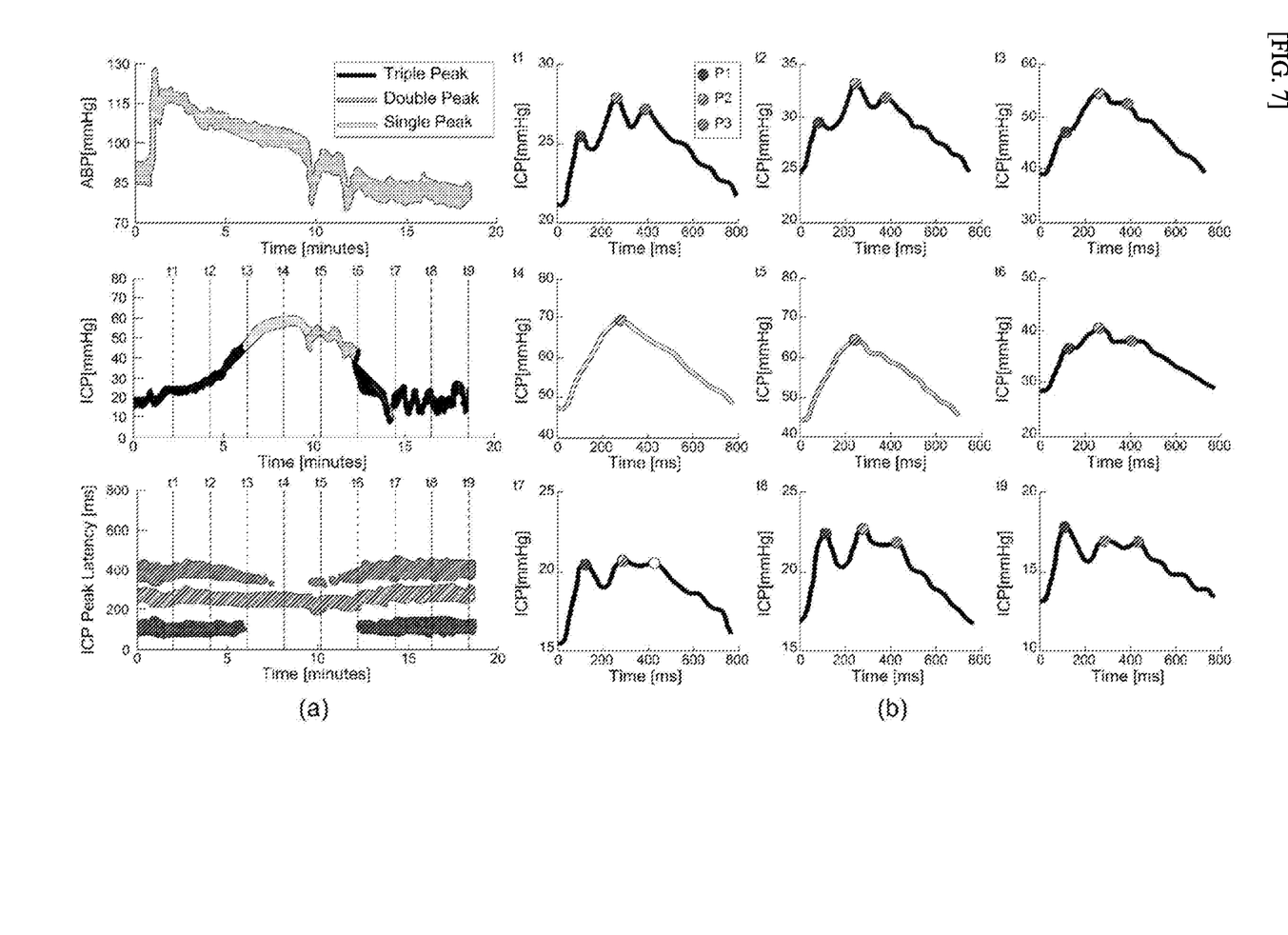
FIGS. 7A and 7B (collectively referred to herein as "FIG. 7") illustrate an example of a peak extracting method of an ICP waveform using a morphological feature of an arterial blood pressure waveform.

FIG. 7 illustrates an example of peak extraction of an ICP waveform using a morphological feature of an arterial blood pressure waveform.

Figure 8:
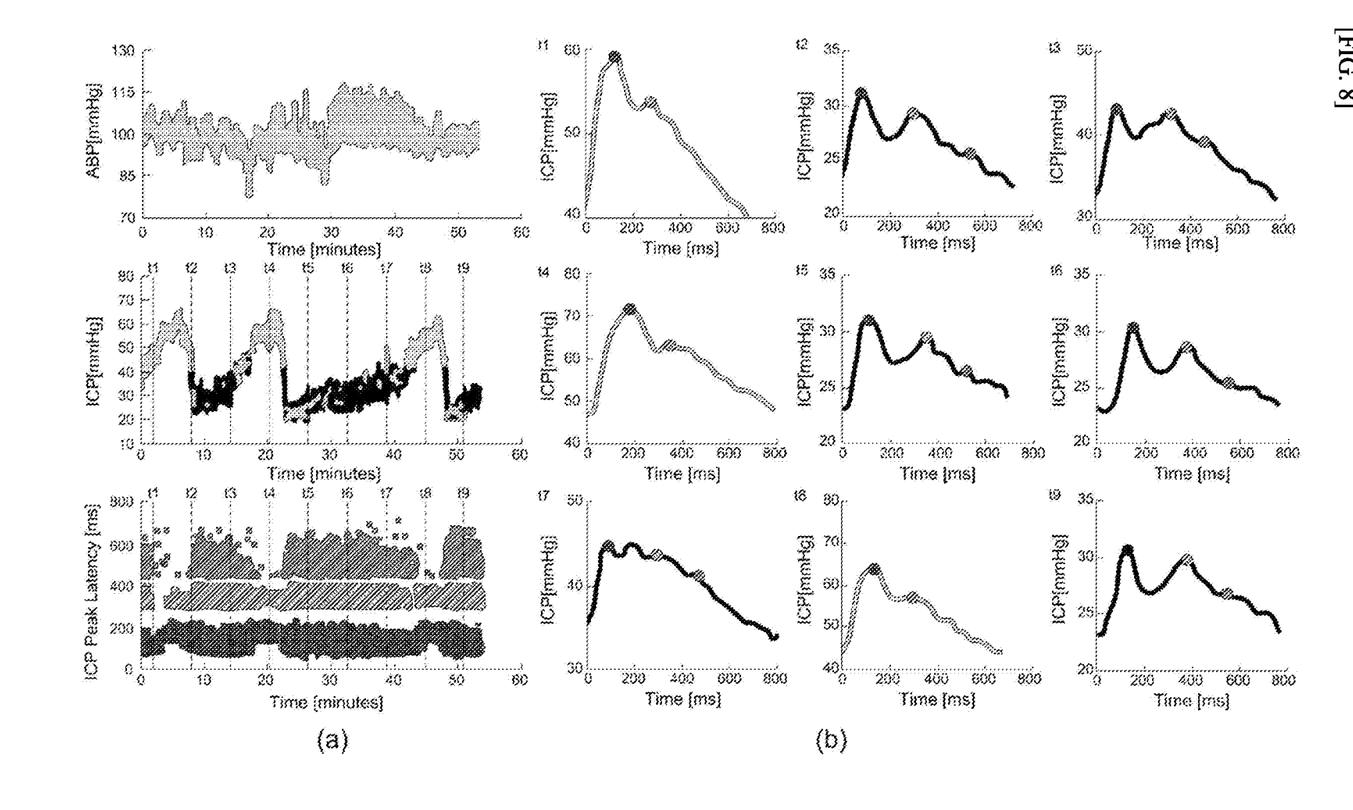
FIGS. 8A and 8B (collectively referred to herein as "FIG. 8") illustrate another example of peak extraction of an ICP waveform using a morphological feature of an arterial blood pressure waveform.

FIG. 8 illustrates another example of peak extraction of an ICP waveform using a morphological feature of an arterial blood pressure waveform.

In FIGS. 7A and 8A, an arterial blood pressure waveform, an ICP waveform, and a clustering result for three peaks of the ICP waveform are illustrated. A vertical axis of a clustering graph for three peaks of the ICP waveform represents a latency from the pulse onset to each peak in the unit of ms. Referring to FIGS. 7B and 8B, it is confirmed that the P1, P2, and P3 peaks assigned as a result of clustering of FIG. 7A are denoted on various waveforms which are measured at actual arbitrary timings.

As described in the peak extracting method of an ICP waveform, it is confirmed that in some waveforms, P2 peak is extracted according to a latency of a peak which is observed first or a position of the dicrotic notch of the corresponding arterial blood pressure waveform. Further, when there is no peak corresponding to each cluster, the flat is extracted as P1, P2, or P3 instead of the peak.

Figure 9:
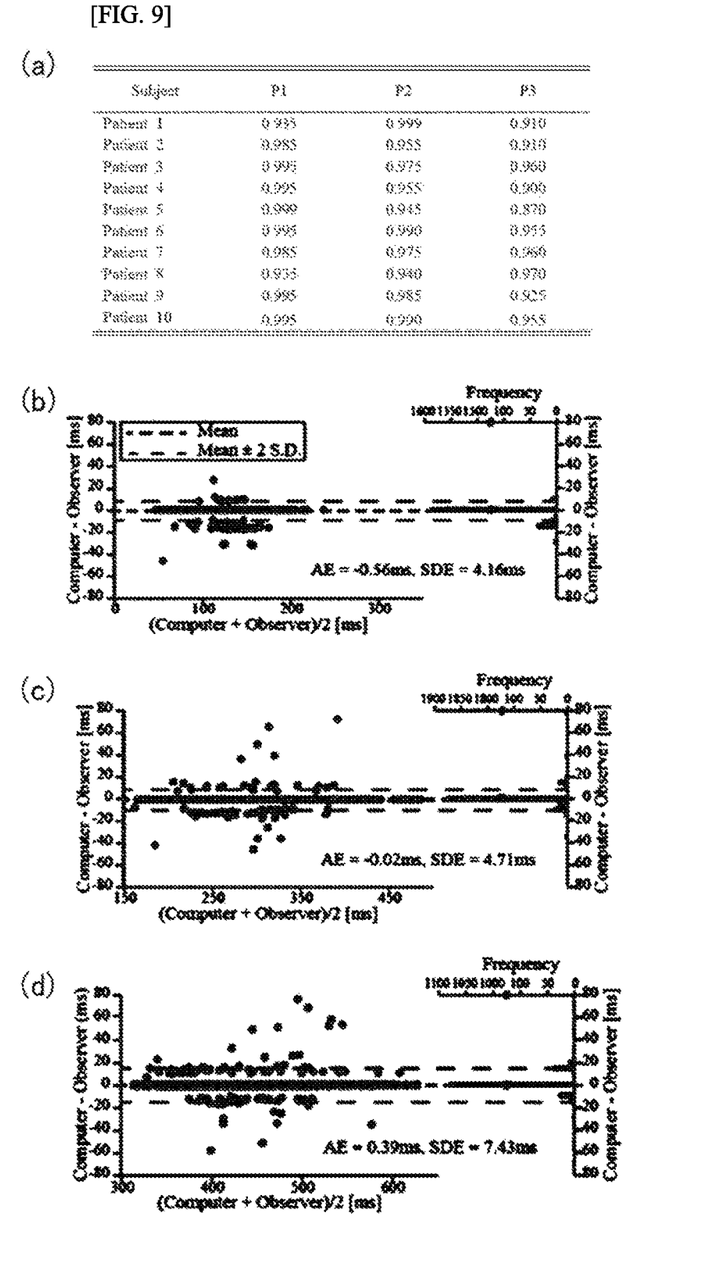
FIGS. 9A, 9B, 9C and 9D (collectively referred to herein as "FIG. 9") illustrate an accuracy verification result of peak extraction of an ICP waveform using a morphological feature of an arterial blood pressure waveform.

FIG. 9 illustrates an accuracy verification result of peak extraction of an ICP waveform using a morphological feature of an arterial blood pressure waveform.

A peak extracting accuracy of the present solution is measured for each of three peaks P1, P2, and P3. For data of ten patients used as an example, two hundred pulses are randomly extracted. An experienced observer manually marked P1, P2, and P3 peaks for a total of two thousand pulses. In this case, the result value of extracting the P1, P2, and P3 obtained by the peak extracting method of an ICP waveform using a morphological feature of an arterial blood pressure waveform was not exposed to the observer. Next, a difference of absolute values of a measurement time of each manually selected peak and a measurement time of an automatically detected peak for one pulse is calculated as an error and an error which is 30 ms or less was ignored.

By the above-described method, accuracies of 98.2%, 97.1%, and 94.5% were calculated for P1, P2, and P3. Further, average errors for latencies of P1, P2, and P3 peaks were −0.56 ms, −0.02 ms, and 0.39 ms, respectively. In the Z-test which is performed to verify a significance of the above error, a significant probability (p-value) of P1 was 0.99, a p-value of P2 was 0.67, and a p-value of P3 was 0.32. When it is interpreted based on the fact that a statistically significant significance value is usually 0.05 or lower, this means that the error in the accuracy verification is not significant. In other words, this means that the peak assigned by the peak extracting method of an ICP waveform using a morphological feature of an arterial blood pressure waveform is not significantly different from the peak assigned by the experienced observer. As a result of calculating a standard deviation of an error (SDE) for every peak, the SDEs were 4.16 ms at P1, 4.71 ms at P2, and 7.43 ms at P3. According to a paper in 2008 by Hu, X et al., it is interpreted that when an SDE value is less than 10 ms for a peak recognition function, the accuracy is high.

In the meantime, the present solution may be implemented as a recording medium including a command which is executed by a computer such as a program module which is executed by the computer. The computer readable medium may be an arbitrary available medium which is accessed by a computer and includes all of a volatile and non-volatile medium, a removable and non-removable medium. Further, the computer readable medium may include all of a computer storage medium and a communication medium. The computer storage medium includes a volatile and non-volatile medium, and a removable and non-removable medium which are implemented by an arbitrary method or technique for storing information such as a computer readable command, a data structure, a program module, and other data. The communication medium includes a typical computer readable command, a data structure, a program module, or other data of a modified data signal such as a carrier wave or other transmitting mechanism and also includes an arbitrary information transfer medium.

The peak extracting device of an ICP waveform using a morphological feature of an arterial blood pressure waveform may be implemented as a computer readable code in computer readable recording media. The recording medium which is capable of being read by computer includes all kinds of recording media in which data, which are capable of being read by a computer system, are stored. For example, the recording medium may include a read only memory (ROM), a random access memory (RAM), a magnetic tape, a magnetic disk, a flash memory, and an optical data storage device. Further, the computer readable recording media are distributed on computer systems connected through the computer communication network, and thus the computer-readable recording media may be stored and executed as the readable code by a distribution scheme.

The above-description is illustrative only and it is understood by those skilled in the art that the present solution may be modified to a specific type without changing the technical spirit of an essential feature of the present solution. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present solution is represented by the claims to be described below rather than the detailed description, and it is to be interpreted that the meaning and scope of the claims and all the changes or modified forms derived from the equivalents thereof come within the scope of the present solution.

The invention claimed is:

1. A peak extracting method of an intracranial pressure (ICP) waveform using a morphological feature of an arterial blood pressure (ABP) waveform, the peak extracting method comprising:
    extracting an ICP pulse onset from a continuous ICP waveform based on a systolic peak of the ABP waveform;
    dividing individual ICP waveforms in the continuous ICP waveform based on the ICP pulse onset;
    deriving a derivative value from each of the individual ICP waveforms to extract an ICP peak, an ICP trough, and an ICP flat;
    calculating latencies from the ICP pulse onset extracted in each of the individual ICP waveforms to cluster ICP peaks with a similar time interval and generate an ICP peak cluster;
    searching an ICP notch from each of the individual ICP waveforms based on a latency of an ABP dicrotic notch of the ABP waveform; and
    extracting P1, P2, and P3 peaks from the individual ICP waveforms by referring to the ICP notch.

2. The peak extracting method of claim 1, further comprising:
    extracting the systolic peak from a continuous ABP waveform;
    extracting an ABP pulse onset of the continuous ABP waveform based on the systolic peak of the continuous ABP waveform;
    dividing the continuous ABP waveform into individual ABP waveforms based on the ABP pulse onset;
    extracting an ABP peak, an ABP trough, and an ABP flat from each of the individual ABP waveforms; and
    extracting the ABP dicrotic notch from the ABP trough.

3. The peak extracting method of claim 1, further comprising:
    after the dividing of individual ICP waveforms in the continuous ICP waveform,
    filtering the individual ICP waveforms by comparing the ICP pulse onset with a threshold onset.

4. The peak extracting method of claim 1, further comprising:
    after the extracting of P1, P2, and P3 peaks from the ICP waveform, analyzing amplitudes of the P1, P2, and P3 peaks to determine a prognosis of a patient with a brain damage.

5. The peak extracting method of claim 1, further comprising:

after the extracting of P1, P2, and P3 peaks from the ICP waveform, analyzing a latency from the pulse onset of the ICP waveform to the P1, P2, and P3 peaks to determine a prognosis of a patient with a brain damage.

6. The peak extracting method of claim 1, further comprising:

after the extracting of P1, P2, and P3 peaks from the ICP waveform, analyzing numbers of the P1, P2, and P3 peaks extracted from the ICP waveform to determine a prognosis of a patient with a brain damage.

7. The peak extracting method of claim 4, wherein the prognosis of the patient with the brain damage is to determine whether an intracranial compliance of the patient with the brain damage is deteriorated or cerebral autoregulation of the patient with the brain damage is normal.

8. The peak extracting method of claim 1, wherein the extracting of the ICP pulse onset from the continuous ICP waveform includes:

calculating a maximum value, a minimum value, and a mean value of a pressure value of the ICP waveform existing between a measurement time of a j-th systolic peak and a measurement time of a j+1th systolic peak of the arterial blood pressure waveform; and extracting a trough of the ICP waveform which satisfies Equation 1 as a pulse onset of the ICP waveform in a time reverse order from a measurement time of the ICP waveform at a point where the maximum value is measured to the measurement time of the j-th systolic peak measurement time, $$|P_{I,k}-\min P_I|<|P_{I,k}-\operatorname{mean}P_I| \quad \text{[Equation 1]}$$

Here, $P_{I,j}$ is a pressure value of the ICP waveform, $\min P_I$ is a minimum value of the pressure value of the ICP waveform, $\max P_I$ is a maximum value of the pressure value of the ICP waveform, and $\operatorname{mean}P_I$ is a mean value of the pressure value of the ICP waveform.

9. The peak extracting method of claim 1, wherein the deriving of the derivative value from each of the ICP waveforms to extract the ICP peak, the ICP trough, and the ICP flat includes:

normalizing data of the ICP waveform;

deriving the derivative value from the normalized ICP waveform; and extracting the ICP peak, the ICP trough, and the ICP flat based on the derivative value.

10. The peak extracting method of claim 1, wherein in the searching of the ICP notch from each of the individual ICP waveforms, a measurement time interval from the ICP pulse onset of the ABP waveform to the ABP dicrotic notch is calculated to extract the ICP trough which is closest to a timing obtained by adding the measurement time interval of the ABP dicrotic notch to the ICP pulse onset as the ICP notch.

11. The peak extracting method of claim 1, further comprising:

sorting the ICP peak clusters in an ascending or descending order.

12. The peak extracting method of claim 1, wherein the extracting of P1, P2, and P3 peaks from the individual ICP waveforms includes:

when the ICP notch is found from each of the individual ICP waveforms, extracting the P1 peak from the ICP peak cluster having a small mean value;

extracting the ICP peak existing before the ICP notch of the ICP waveform as the P2 peak; and extracting the ICP peak existing after the ICP notch of the ICP waveform as the P3 peak.

13. The peak extracting method of claim 1, wherein the extracting of P1, P2, and P3 peaks from the individual ICP waveforms includes:

when the ICP notch is not found from each of the individual ICP waveforms, sorting clusters in an ascending order from the ICP peak cluster having a small mean value;

extracting the ICP peak assigned to a first cluster according to the sorted order as the P1 peak;

extracting the ICP peak assigned to a second cluster as the P2 peak; and extracting the ICP peak assigned to a third cluster as the P3 peak.

14. The peak extracting method of claim 12, wherein when a mean time interval between the ICP peak assigned to the first cluster and the ICP pulse onset of the continuous ICP waveform is 200 ms or longer, the ICP peak assigned to a first cluster is extracted as the P2 peak.

15. The peak extracting method of claim 12, wherein when any one of P1, P2, and P3 is not extracted from each of the individual ICP waveforms, any one of the ICP flats is extracted as the ICP peak which is not extracted.

16. A non-transitory computer readable medium in which a program for executing the peak extracting method of an ICP waveform of claim 1 is recorded.

* * * * *